United States Patent
Shaunnessey

Patent Number: 5,823,941
Date of Patent: Oct. 20, 1998

[54] APPARATUS FOR DIRECTING THE MOVEMENT OF AN ENDOSCOPIC SURGICAL LASER ESPECIALLY FOR USE IN VAPORIZING BRAIN TUMORS

[76] Inventor: Jerome Shaunnessey, 910 Southbridge Dr., Aurora, Ill. 60506

[21] Appl. No.: 553,767

[22] Filed: Oct. 23, 1995

[51] Int. Cl.⁶ ............................................. A61B 17/36
[52] U.S. Cl. ............................ 600/108; 606/17; 606/18
[58] Field of Search .................... 606/7, 13–19; 600/108

[56] References Cited

U.S. PATENT DOCUMENTS

| | | | |
|---|---|---|---|
| 3,865,113 | 2/1975 | Sharon et al. | 606/18 |
| 4,638,800 | 1/1987 | Michel | 606/18 |
| 5,163,935 | 11/1992 | Black et al. | 606/17 |
| 5,454,807 | 10/1995 | Lennox et al. | 606/15 |
| 5,474,449 | 12/1995 | Loge et al. | 606/19 |
| 5,558,670 | 9/1996 | Konwitz et al. | 606/18 |

*Primary Examiner*—Michael Peffley

[57] ABSTRACT

An apparatus for removing brain tumors by vaporizing the tumor tissue with a laser beam in select scan planes of the tumor. A cored hole through the tumor is made by the laser beam, and an endoscope is inserted through the cored hole, which has a mirror mounted at a 45 degree angle near the end of it and mounted within it, that is capable of reflecting the laser beam at a 90 degree angle. The endoscope is inserted all the way through the cored hole, and sucessive scans of the brain tumor are taken perpendicular to the endoscope. The endoscope is then moved axially to position the 45 degree mirror at each scan plane, and the reflected laser beam is then rotated and also oscillated between calculated angles to vaporize the tumor tissue in each scan plane, until the entire brain tumor is vaporized by the laser beam. During this procedure the gas being produced by vaporization of the tumor tissue is suctioned out through the interior of the endoscope.

11 Claims, 8 Drawing Sheets

DISCRETE SCAN PLANES

APPARATUS FOR DIRECTING THE MOVEMENT OF AN ENDOSCOPIC SURGICAL LASER ESPECIALLY FOR USE IN VAPORIZING BRAIN TUMORS

BACKGROUND OF INVENTION

Many brain tumors are inoperable because of their location in the brain, and therefore, can not be removed without causing the death of the patient or resulting in unacceptable neurological damage. As a result, the prognosis for such patients is poor. Presently, approaching such tumurs is risky, and if they are tried to be reached by present day techniques, the operation is usually quite long and very complicated. And if the surgeon is sucessful in removing the tumor, the patient has went thru a massive operation on his or her brain, which often times leaves them with considerable neurological damage.

Accordingly, it is a general object of this invention to propose a inovative mechanism and technique to eliminate the foregoing disadvantages. Another object is to provide a method for removing brain tumors without actually performing a crainiotomy. Another object is to provide a method for reaching brain tumors that were previously un-reachable. Another objective is to simplify and reduce the time it takes to perform a brain operation. A particular objective is to reduce the risk of brain surgery and the neurological damage it can cause to patients. These and other objectives will become apparent from the following detailed description and accompanying sheets of drawings.

BRIEF DESCRIPTION OF THE DRAWINGS

FIG. 11b is a profile of scan plane 10 shown in FIG. 11a.

SUMMARY OF THE INVENTION

Briefly described, the present invention contemplates a novel and unique mechanism for irradicating brain tumors situated deep within the brain. The mechanism is relatively simple, it is comprised of essentially two elements; a slim tube or endoscope for probing into the brain, and a slim guide tube that the endoscope fits inside of. The guide tube is of sufficient length to be inserted into the brain up to the tumor in question, and also project above the skull a suitable distance. The endoscope has a distal end and a caudal end. At the caudal end is a source for producing a thin beam of Laser light capable of destroying living tissue, which is aligned thru the center of the slim tube or Endoscope. Also at the caudal end, separate means are provided for both moving the endoscope axially within the guide tube and rotating the endoscope within the guide tube. At the distal end of the Endoscope, and suitably mounted within the Endoscope is a 45 degree corner reflector capable of reflecting the Laser beam at a 90 degree angle. Destruction of the tumor is accomplished by taking CAT or MRI scans of the tumor in planes perpendicular to the endoscope, and positioning the 45 degree corner reflector in one of the CAT or MRI scan planes, then rotating the reflected Laser beam to destroy the tumor tissue in that particular plane. The reflected Laser beam can be rotated continually or be instructed to only oscillate between some angle. Complete destruction of the tumor is accomplished by moving the corner reflector to successive planes. The entire process is accomplished by digital computer analysis of the profile of each individual CAT or MRI scan, then using this information to direct the positioning and rotation or oscillation of the 90 degree reflected Laser beam to destroy the tumor tissue in that particular scan plane.

DESCRIPTION OF THE PREFERRED EMBODIMENT

Figure 1:
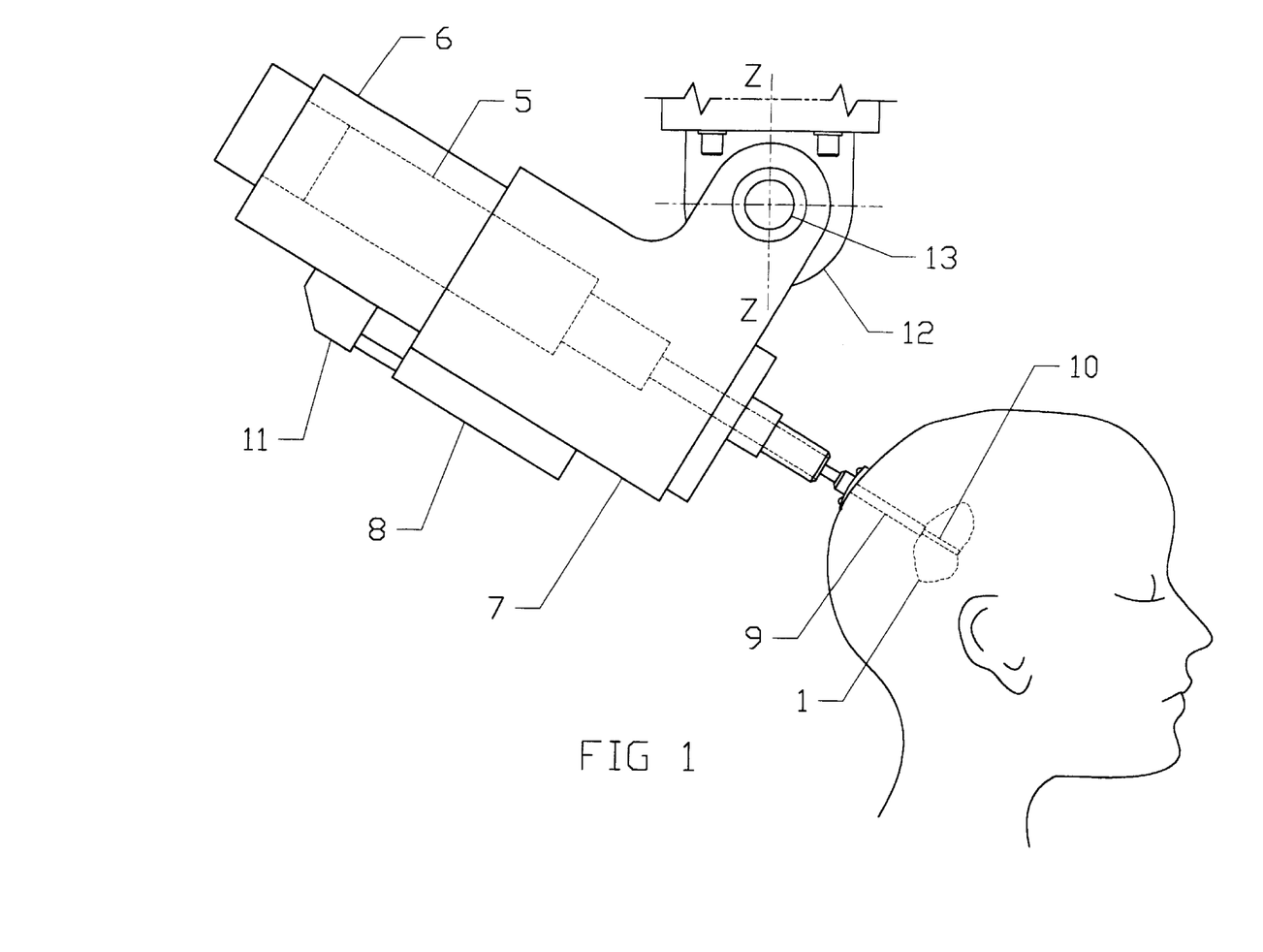
FIG. 1 is a elevation of the apparatus for positioning and operat-the 'Endoscopic Surgical Laser'.

FIG. 1, is a plan view of the Endoscopic Surgical Laser, and is shown in a typical operative position relative to tumor 1, of the patient. The complete endoscopic surgical laser assembly is mounted above the patient as shown in FIG. 1, and is provided with a means for positioning the assembly at any point in a horizontal plane relative to the head of the patient, and can be raised up and down, and also rotated about axis Z—Z. The Endoscopic Surgical Laser is mounted within carrier frame 6, as shown in FIG. 1, and is slidable on suitable guides within pivotable saddle 7. Carrier frame 6, is advanced and retracted by linear digital positioner 8, suitably mounted within pivotable saddle 7, which is connected to carrier frame 6, by clevis 11. Pivotable saddle 7, is pivotably mounted on shaft 13, as shown in FIG. 1, and is angularly positioned by digital pulse motor 12. With this arrangement, the Endoscopic Surgical Laser may be positioned within a 360 degree horizontal plane, and at any angle between approximately 45 degrees below the horizontal and 90 degrees above the horizontal.

Figure 2:
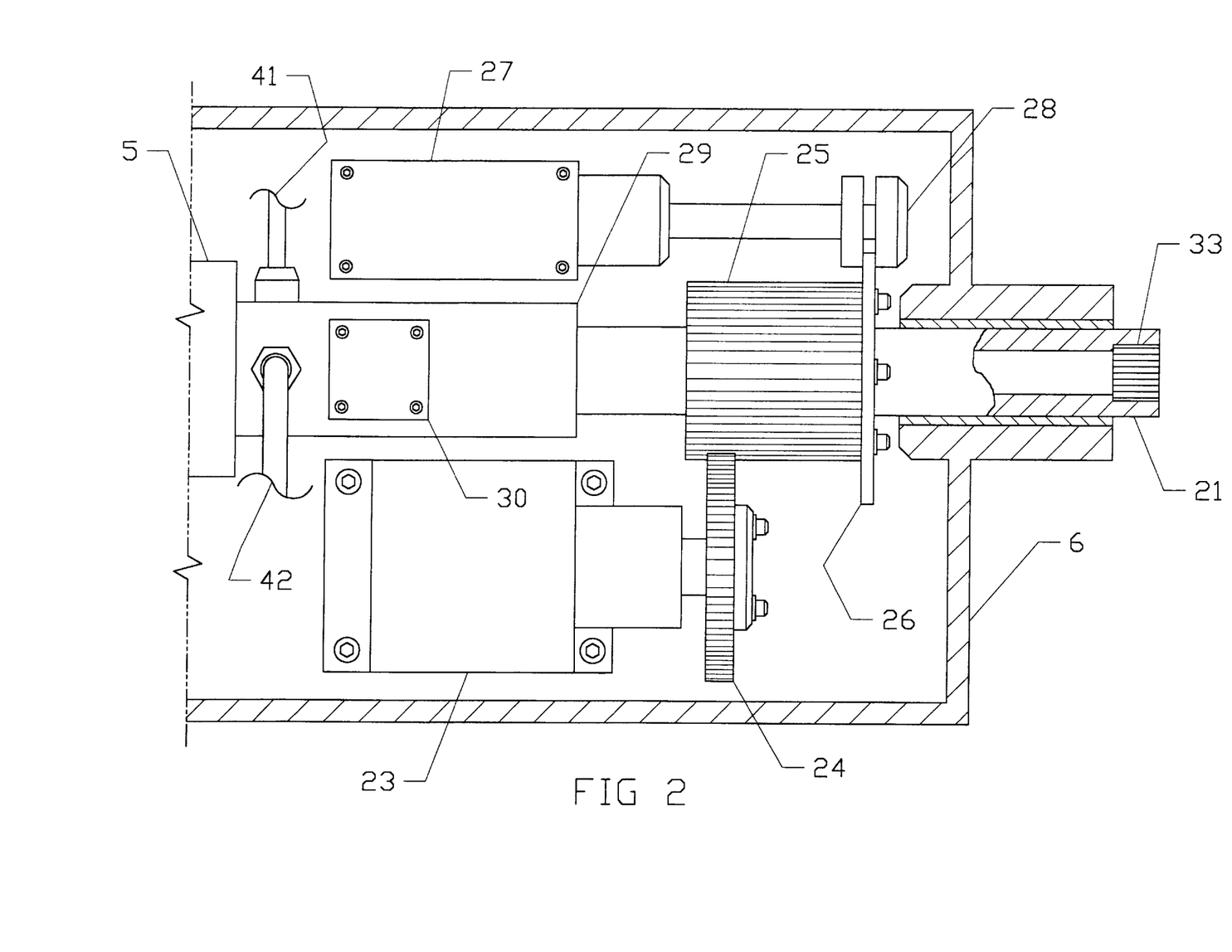
FIG. 2 is a schematic sectional view of the mechanism for rotating the endoscope and moving it axially.
Figure 7:
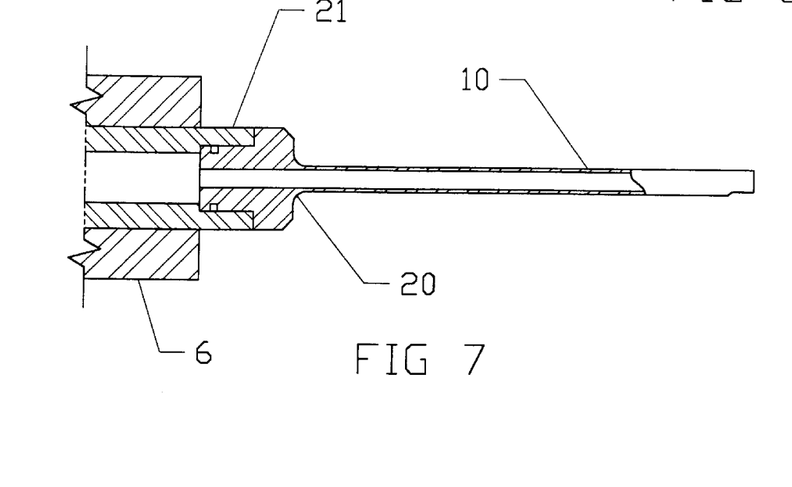
FIG. 7 is a sectional view thru the endoscope.
Figure 8:
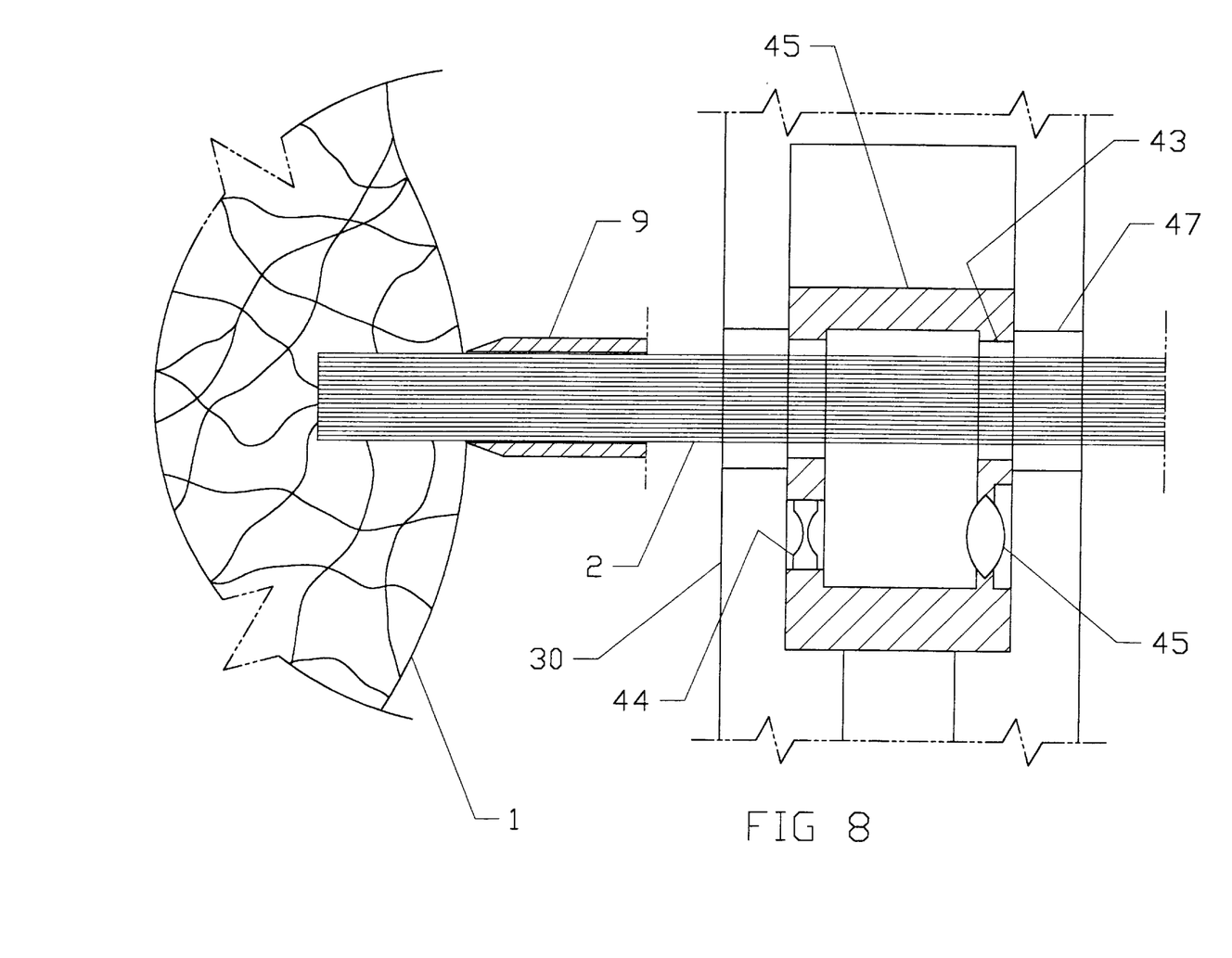
FIG. 8 is a illustration of the tumor core vaporization by the laser beam and the collimater shutter box position.
Figure 9:
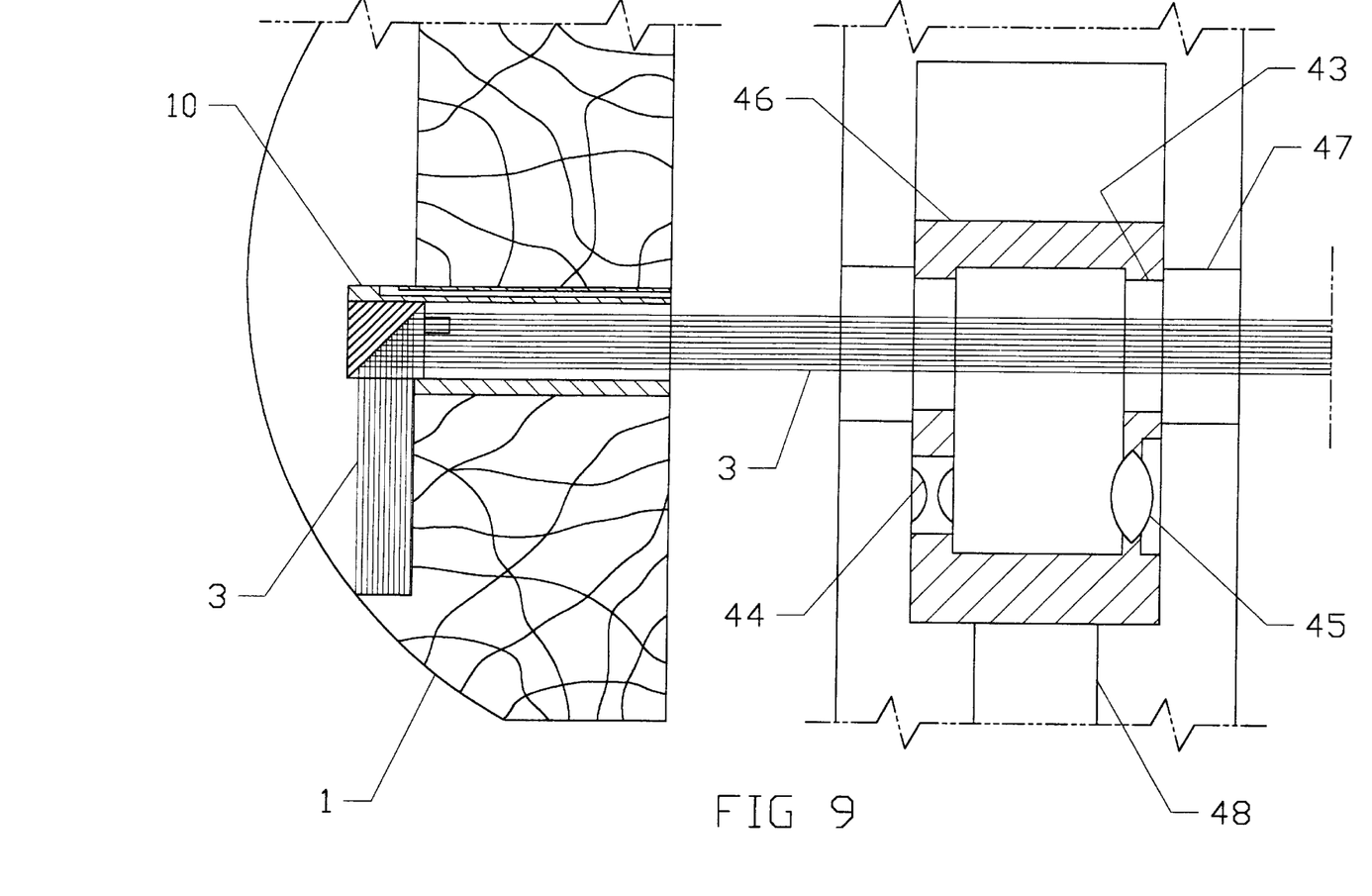
FIG. 9 is a illustration of tumor vaporization by the reflected laser beam and the collimater shutter box position.

Referring now again to FIG. 1, laser head 5, is mounted within carrier frame 6, and tubular extension 29, shown in FIG. 2, extends from the exit aperture of the laser head, and is provided with an optical shutter arrangement within it, for producing two different sizes of collimated laser beams. One laser beam is about the same diameter as the outside diameter of endoscope 10, shown in FIG. 7, and is indicated in FIG. 8, as laser beam 2. The other laser beam is approximately one half the diameter of laser beam 2, and is indicated in FIG. 9, as laser beam 3. Slidable and rotatable within tubular extension 29, is actuator tube 21, which incorporates female adapter 33, shown in FIG. 2. With endoscope 10, installed in the adapter end of actuator tube 21, the optical axis of the laser beam is coaxial with the longitudinal axes of tubular extension 29, actuator tube 21, and endoscope 10. Suitable controls are also provided to control the power output and pulse rate of the laser beam.

Referring now to FIG. 2, the mechanism for rotating endoscope 10, and moving the endoscope axially is illustrated. A rotary stepping motor 23, has a shaft extending from it, and gear 24, is suitably mounted on it. This gear 24, engages gear 25, which has a face width somewhat longer then the face width of gear 24, so that gear 25, can slide axially relative to gear 24. The ratio between the two gears; 24, and 25, is 1:1. Electrical pulses to stepping motor 23, will rotate gear 24, to cause gear 25, to rotate in the opposite direction, which will cause endoscope 10, to rotate with discrete motion. Gear 25, is integral with actuater tube 21, and is moved axially forward and backward by linear digital pulse actuator 27, which has clevis 28, suitably mounted on the end of the actuator shaft of actuator 27. Disc 26, is suitably attached to gear 25, and is somewhat larger in diameter then the outside diameter of gear 25. Clevis 28, engages disc 26, and disc 26, is rotatable within clevis 28, which engages both sides of disc 26. With this arrangement, endoscope 10, mounted at the nose end of actuator shaft 21, can be moved axially, and rotated or oscillated with exact precision.

Figure 3A:
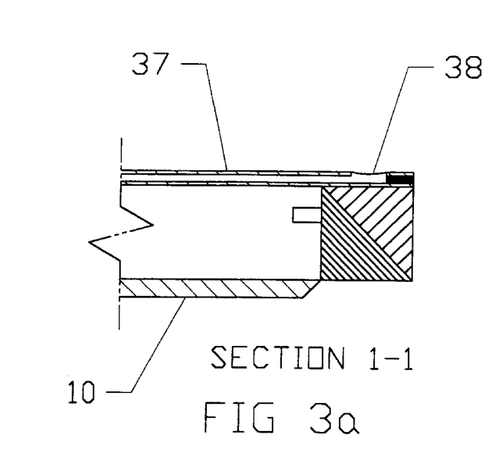
FIG. 3a is a sectional view of the distal end of the endoscope taken thru section 1-1 of FIG. 3c.
Figure 3B:
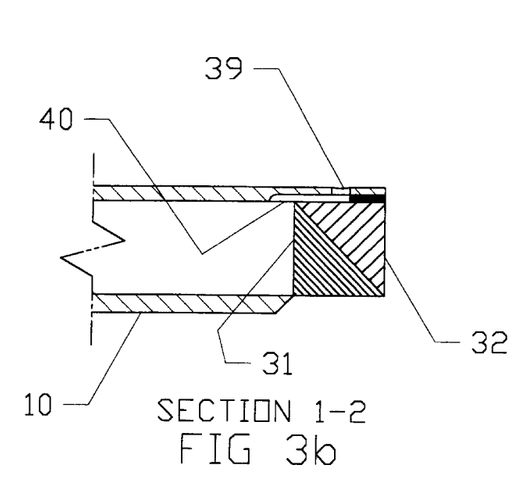
FIG. 3b is a sectional view of the distal end of the endoscope taken thru section 1-2 of FIG. 3c.
Figure 3C:
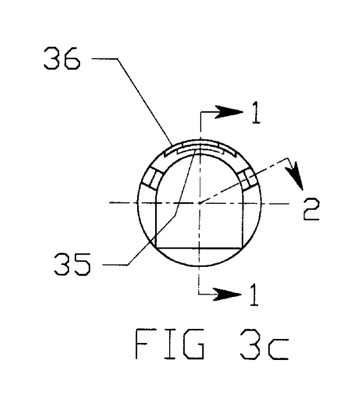
FIG. 3c is an end view of the endoscope.

Referring now to FIGS. 3a and 3b, which illustrates sectional views of the distal end of endoscope 10. At the distal end, and mounted within it is 45–90–45 degree plastic optical prism 31. The shape of prism 31, is best illustrated by referring to the end view of endoscope 10, shown in FIG. 3c, which illustrates that one half of the profile of prism 31, is semicircular with flat sides extending from the semicircular half to a flat side that lies in a plane coincident with the radius of the semicircular section, and the circular profile of the inside diameter of endoscope tube 10, intersects the profile of the end of prism 31. The end of endoscope 10 is slotted as shown in end view FIG. 3c of endoscope 10, to accomodate prism 31, which is cemented into the slotted end of endoscope 10. Behind prism 31 is backup piece 32, which is similar in shape to prism 31, and is made of a nontransparent plastic. Backup piece 32, is also cemented into the end of endoscope 10, as shown in FIG. 3b.

Because the Laser beam vaporizes living tissue, a carbon dioxide gas is produced. Continual removal of this gas is provided by producing a differential in pressure between the inlet to the tumor cavity and the outlet to the tumor cavity. This differential in pressure will serve two purposes, one it will maintain a constant pressure within the tumor cavity, which will serve to prevent the tumor cavity from collapsing during the vaporizing of the tumor, and secondly, it will produce a continual flow of the pressurizing gas for removal of the carbon dioxide gas being produced. The tumor cavity being produced by vaporizing the tumor, is communicated with by inlet port 38, and outlet ports 39, shown in sections 1-1 and 1-2, of FIG. 3c, of endoscope 10. The pressurized gas is preferably helium because of it's coolant properties, and is supplied to the tumor cavity thru passage 37, and port 38, as shown in section 1-1 of FIG. 3, and exhausted thru ports 39, and passages 40, shown in section 1-2. Passage 37, is formed in the wall of the endoscope tube by cutting two grooves in the outer wall of the endoscope tube, as best seen in the end view of endoscope 10. The outer groove is somewhat wider then the lower groove, and the thin circular segment 36, shown is cemented into the outer groove to form passage 37. Passages 40, are formed in the inner wall of the endoscope tube by cutting two slots angularly spaced, as shown in the end view of endoscope 10, which extend from the distal end of the tube back past prism 31, to form the inlets to passages 40. Pressurized gas is supplied to passage 37 by supply port 42, shown in FIG. 2, which communicates with passage 37, thru the wall in laser head extension 29, and a passage provided with suitable seals in actuator tube 21. The exhaust port for maintaining downstream pressure is also shown in FIG. 2, and is indicated as port 42, which communicates directly with the inside of laser head extension 29, which then communicates with the inside of actuator tube 21, and the inside of endoscope 10, whereby, the differential pressure across Ports 41, and 42, produce a constant pressure within the tumor cavity being created, and a constant flow thru the tumor cavity, whereby, the carbon dioxide gas being produced is continually suctioned out of the tumor cavity thru outlet port 41.

Figure 4A:
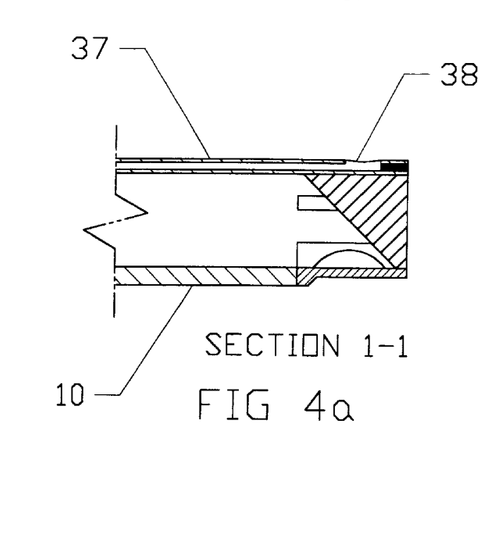
FIG. 4a is a sectional view of the distal end of an alternate endoscope taken thru section 1-1 of FIG. 4c.
Figure 4B:
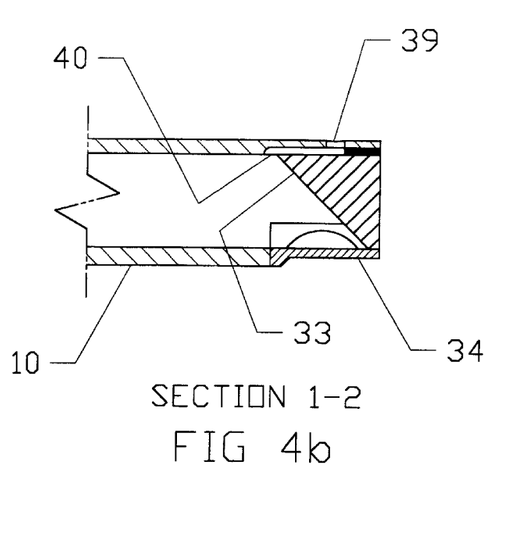
FIG. 4b is a sectional view of the distal end of an alternate endoscope taken thru section 1-2 of FIG. 4c.
Figure 4C:
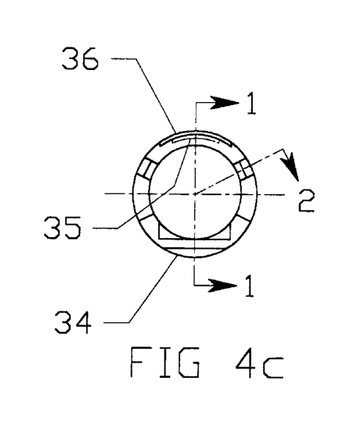
FIG. 4c is an end view of an alternate endoscope.

FIGS. 4a, 4b, 4c, illustrates an alternate design for the end of endoscope 10, which has essentially the same construction as the end of endoscope 10, previously described, except that reflector 33, shown in FIGS. 4a and 4b, is used instead of prism 31. Reflector 33, is a round bar of nontransparent plastic with a flat surface angularly disposed at 45 degrees to it's axis. The 45 degree surface is coated with a nonmetallic reflective coating, and reflector 33, is then cemented into place as shown in FIGS. 4a and 4b. For transmitting the reflected laser beam to the exterior of the endoscope tube, a transparent shield 34, is provided, and is best illustrated in the end view of endoscope 10, of FIG. 4c. Transparent shield 34, is a circular segment that has the same inside and outside diameter as the endoscope tube, but has a flat circular surface cut in it's inside diameter that is disposed at an angle of 45 degrees from the 45 degree reflector surface of reflector 33, and has another flat surface cut on the outside of transparent shield 34, parallel to this inside surface, forming a transparent window for the reflected laser beam to pass thru. Transparent shield 34, serves to seal the inside of endoscope 10, from moisture, and is cemented into the angular slot cut in the end of the endoscope.

Figure 10:
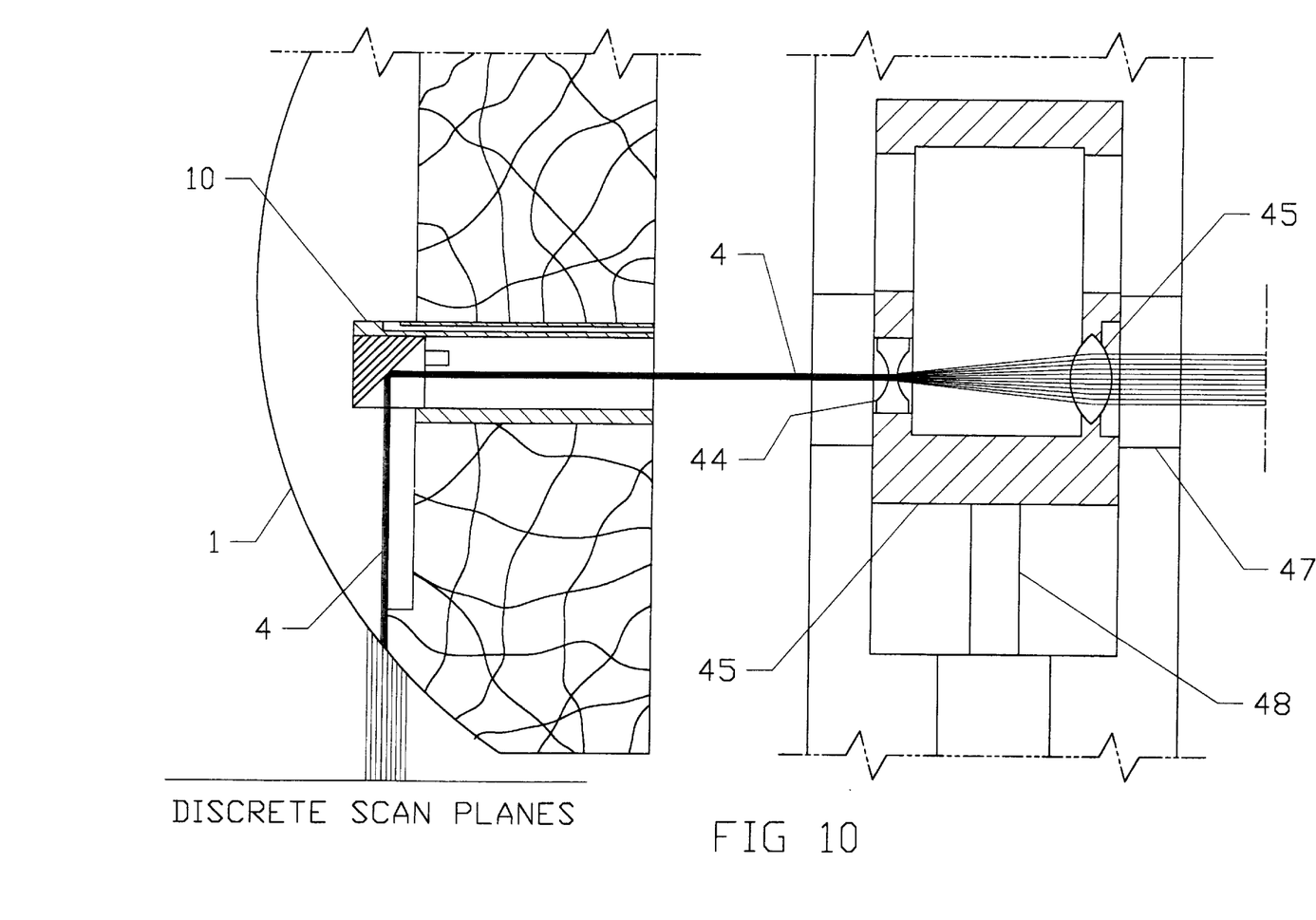
FIG. 10 is an illustration of the discrete reflected laser beam and the collimater shutter box position.

Aside from producing the two different size laser beams 2, and 3, previously mentioned, an additional optical lens shutter box 30, is also provided within laser head extension tube 29, as indicated in FIG. 2, and is best illustrated in FIGS. 8, 9, and 10. The optical lens shutter box 30, has aperture 47, which extends thru it, and is somewhat larger then laser beam 2, previously mentioned. Housed within optical lens shutter box 30, is lens shutter 46, which has an aperture 43, thru it for allowing both laser beams 2, and 3, to pass thru it, as shown in FIGS. 8, and 9. A pair of optical lens for collimating laser beam 3, is also suitably mounted within lens shutter 41, and is comprised of two optical lens, 44, and 45. as shown in FIG. 8. Lens 44, is a concave lens, and lens 45, is a convex lens, and are spaced apart at approximately the focal length of convex Lens 45, creating a discrete collimated laser beam as shown in FIG. 10. Shifting of lens shutter 46, is accomplished by energizing actuator 48, from a first position, wherein, the laser beam 2, and laser beam 3, are both able to pass thru aperture 43, as shown in FIG. 8, and FIG. 9. wherein, shifting lens shutter 46, to it's second position causes laser beam 3, to be collimated into discrete laser beam 4, shown in FIG. 10. The diameter of the discrete laser beam is determined by the shape of optical lens 44, and 45, and is chosen to be an equal division of Laser Beam 3. Shifting of lens shutter 41, to the discrete laser beam 4, will also cause the power of the discrete laser beam to be reduced proportionately.

Figure 5:
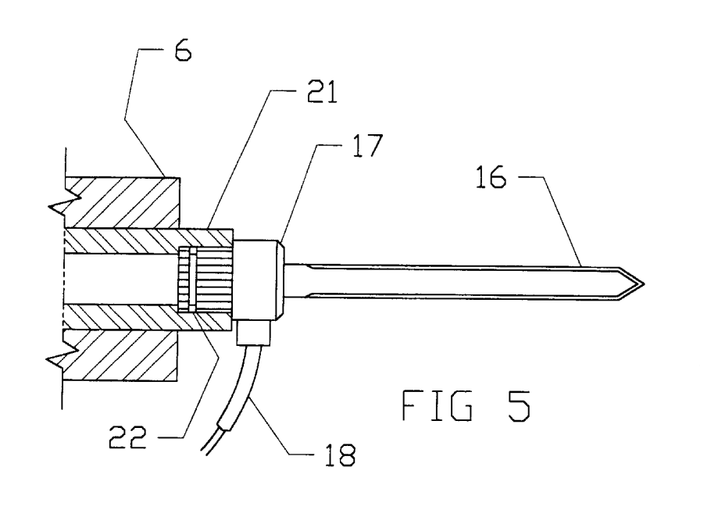
FIG. 5 is a plan view of the incision knife.

Referring now to FIG. 5, incision knife 16, is illustrated, which has two cutting edges, wherein, the width of the knife is slightly larger then the diameter of guide tube 9, and at the caudal end is male adapter end 17, which engages female adapter 33, at the distal end of actuator tube 21. Locking of the male adapter into the female adapter is accomplished by engaging slot 22, either manually or by providing automatic engagement and disengagement thru electromechanical methods. Because it is desirable to prevent bleeding of any small blood vessels that the incision knife severs when cutting thru brain tissue, a means for cauterizing these blood vessels is provided by electrifying incision knife 16, thru electrical connector 18, attached to the caudal end of incision knife 16, as shown in FIG. 5.

Figure 6:
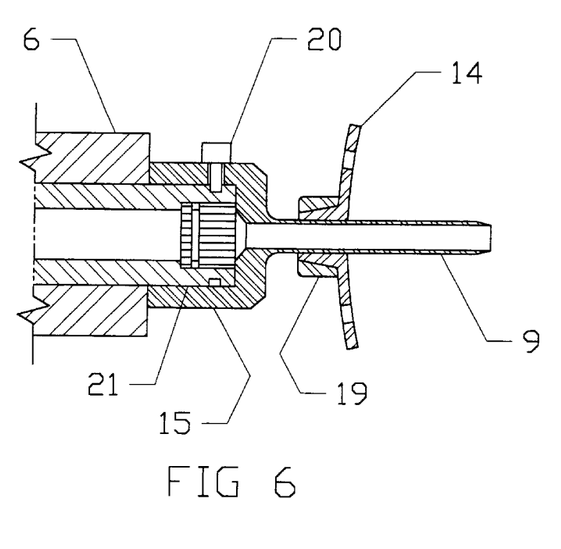
FIG. 6 is a sectional view thru the guide tube and clamp.

FIG. 6, illustrates guide tube 9, which serves as a bearing for endoscope 10, to move axially and rotate within, and also to align and guide endoscope 10. Guide tube 9, is constructed with two integral tubular sections. Toward the distal end is the smaller of these two tubular sections, which has an inside diameter only slightly larger then the outside diameter of endoscope 10, providing a sliding fit between the two. At the caudal end is a larger tubular section 15, which has an inside diameter only slightly larger then the outside diameter of actuator tube 21. Locking guide tube 9, on the end of actuator tube 21, is provided by lock screw 20, which engages a circular groove near the distal end of actuator tube 21, as shown in FIG. 6. Clamp 14, is used to secure the guide tube 9, in place after guide tube 9, has been inserted into the incision made by incision knife 16, and is also illustrated in FIG. 6, which is done either with adhesives or with small screws into the patients skull. After guide tube 9, has been inserted properly in place, lock nut 19, is then tightened to secure clamp 14, to guide tube 9. It should also be noted that the enlarged caudal end of endoscope 10, is the same diameter as the outside diameter of actuator tube 21, which enables the end of actuator tube 21, to also rotate and slide axially within the enlarged tubular section 15, of guide tube 9. It is important to note, that as previously mentioned; both the guide tube 9, and endoscope 10, are made of plastic, to insure that there is no interference when both the guide tube 9, and endoscope 10, are placed in the magnetic field of a Magnetic Resonance Imaging scanner.

BRAIN OPERATION PROCEDURE

The whole brain operation procedure is very dependent upon the accuracy of Computerized Axial Tomography, or Magnetic Resonance Imaging brain scanners. and either one may be employed in this procedure, however, it might be noted, that Magnetic Resonance Imaging scanners can distinguish between tumor tissue and brain tissue, which may be preferable. The first thing that the neurosurgeon does is place a plastic pin in the patient's skull, which will serve as a reference point. The patient is then placed upright on a surgical operating trolly and his or her head is rigidly clamped, and the position of the reference pin placed in the patient's skull is sensed by electromechanical means, and stored in the computer for future use. The next thing the neurosurgeon does is determine the location, size, and shape of the brain tumor, by taking both horizontal and vertical scans of the tumor, from which a three dimensional image of the tumor is created by image processing and computer graphic techniques. From this three dimensional image, he must determine the most optimum line thru the tumor along which to insert the endoscope. The neurosurgeon does this by selecting two points on the periphery of the three dimensional image of the tumor, whereby, an imaginary line is created thru the tumor and the length and angle of this imaginary line is calculated relative to the reference pin placed in the patient's head. This information is then stored by the computer for future use in calculating the position and angle of the Endoscopic Surgical Laser relative to the reference pin. The neurosurgeon must also determine that along this line, the endoscope will be able to irradicate all of the tumor, and must also select this line with consideration for how much brain damage will occur if the endoscope is inserted along this line. Naturally he will try to select the optimum compromise between these two considerations. However, because of the versatility of the Endoscopic Surgical Laser to be positioned at almost any angle, he will have many options at his disposal. When all of these things have been determined, the neurosurgeon may either schedule the operation for a later date while he studies this information, or he can begin the next phase of the operation.

The patient is then moved by trolley back to the Endoscopic Surgical Laser, and the Endoscopic Surgical Laser is automatically positioned at the correct point in space relative to the reference pin. A small burr hole is made in the patient's skull and the dura lining of the brain is opened. The electrical surgical knife is fitted into the adapter end of the actuator tube, and locked in place. The Endoscopic Surgical Laser is automatically positioned coincident with the imaginary line thru the tumor, and the knife is automatically advanced and inserted thru the brain up to the edge of the tumor, and as the knife is being inserted, it is being electrically charged to cauterize any tiny blood vessels that it may sever.

The knife is then withdrawn and removed from the nose of the actuator tube, and the guide tube is then installed on the adapter end of the actuator tube, and locked in place, and then advanced thru the brain the same distance as the incision made by the knife, which is up to the edge of the tumor, as shown in FIG. 1. Clamp 14, is then secured to the patients skull by either adhesives or with small screws to keep it securely in place, and the clamp lock nut is then tightened to secure the clamp to the guide tube.

A biopsy of the tumor can now be taken, which will provide the pathologist with a specimen of the tumor tissue, and may be performed by entering a biopsy needle down thru the guide tube, and removing a specimen of the tumor tissue.

Referring now to FIG. 8, the manner in which the center of the tumor is cored out is illustrated. With the Endoscopic Surgical Laser in the retracted position, the actuator tube is actuated to advance into engagement with the enlarged end of the guide tube. Laser beam 2, will then be activated to begin coreing out a hole thru the tumor, which will be approximately the same diameter as the inside diameter of the guide tube, as shown in FIG. 8. Laser beam 2, will core this hole thru the tumor by firing a number of consecutive pulses, and the carbon dioxide gas being produced will be suctioned directly out of the hole being produced thru the interior of the guide tube, and the actuator tube. The cored hole thru the tumor will serve an important purpose, which is to provide a hole for the endoscope to enter the tumor.

Figure 11A:
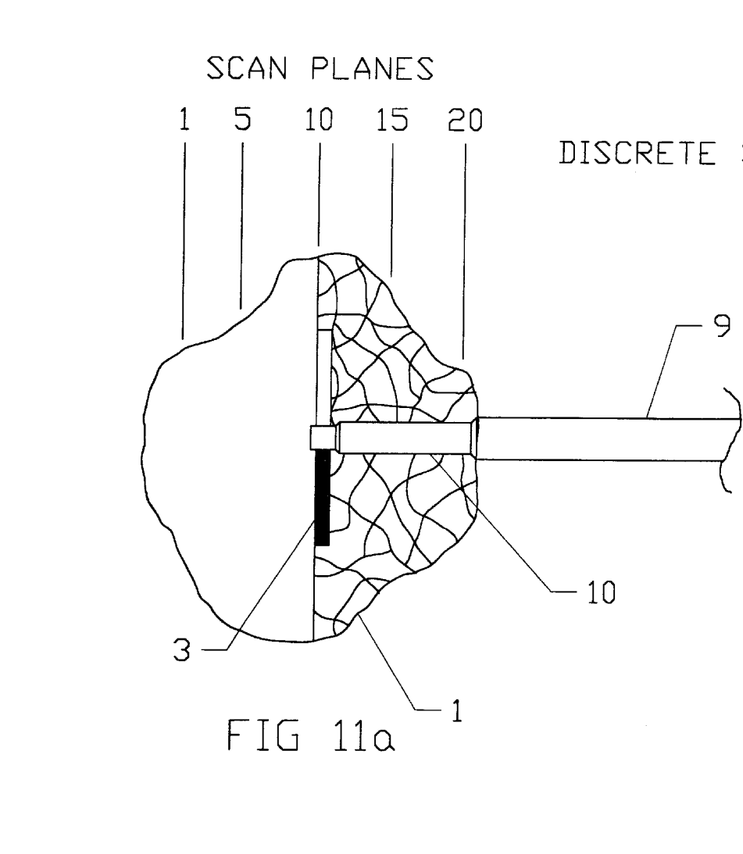
FIG. 11a is a schematic of the scan planes taken thru a tumor.

After this procedure is completed, the actuator tube is withdrawn from the enlarged end of the guide tube and the endoscope is installed in the female adapter of the actuator tube. The endoscope is now advanced and inserted into the guide tube all the way thru the cored hole in the tumor to the position of the first scan plane, which has been predetermined from the three dimensional image of the tumor. The endoscope is left inside of the tumor as shown in FIG. 1, and the patient is moved by trolley to either a CAT or MRI brain scanner. The reason the Endoscope is left within the tumor is to have the scans taken in planes that are relative to the endoscope and exactly perpendicular to the endoscope, starting at the distal end of the endoscope, as shown in FIG. 11a, and at increments that are approximately equal to the width of the reflected laser beam. The profile of each scan of the tumor will be analyzed by image processing techniques, and the manner in which each slice of the tumor will be irradicated will be determined by computer analysis. This information will then be formulated into a computer program and then fed to the digital motors for directing the rotation and linear motion of the endoscope. The depth of the tumor tissue removed by the laser beam is dependent upon the length of time the laser beam is held in one spot. For example, if the laser beam is moved slowly over the tumor tissue, it will destroy or vaporize deeper. If it is moved quickly over the tumor tissue, it will not cut as deeply. Consequently, the speed at which the laser beam rotates or oscillates must also be predetermined, which can be determined from a knowledge of tumor tissue. This data is is then incorporated into the computer program for controlling the speed at which the endoscope rotates or oscillates.

Referring to FIG. 6, the Endoscope is shown halfway entered into the tumor and positioned at scan plane number 10. A full view of scan plane number 10, is also shown. In scan plane 10, the first instruction to the endoscope would be to core out the circular section in the center of scan plane 10. The endoscope would do this by rotating continously at a certain speed, which would vaporize the tumor tissue in a spiral fashion.

Figure 11B:
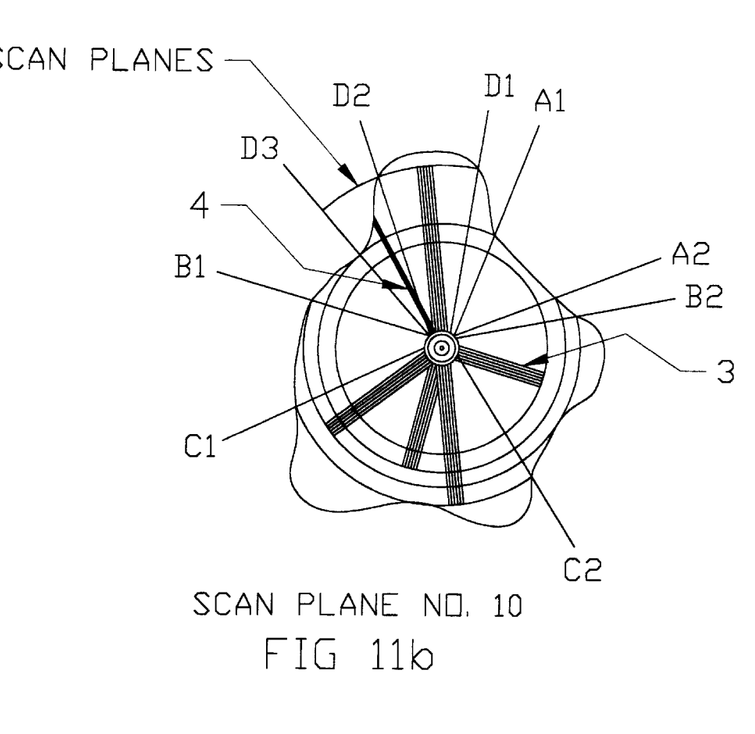

The laser beam would then turn off and be instructed to move to a particular angular position. In scan plane number 10, the endoscope would rotate to angle position A1. The laser beam would then turn on and begin to oscilate between angle A1 and angle A2, and at the same speed as the rotational speed. After this section was vaporized, the beam would turn off, and be instructed to move to angle B1. The beam would then turn on and begin to oscillate between angle B1 and angle B2. This procedure would be repeated for the areas between angles C1 and C2, and angles D1 and D2. After a plane or slice has been destroyed, the endoscope is then commanded to move backwards out of the tumor to the next consecutive scan plane, where it should be pointed out, that it is important for the endoscope to move backwards out of the tumor, since by moving backwards out of the tumor, the endoscope is supporting the tumor and maintaining the profile of the tumor in the same position in which the scans were taken. It should also be noted that while the laser beam is rotating or oscilating within the tumor, the side walls of the tumor are also being cauterized by the edge of the rotating or oscillating laser beam, which prevents bleeding of the tumor into the cavity being created. For those areas which are smaller then the width of the laser beam, the beam is made narrower by actuating the shutter box to switch to laser beam 4, as shown in FIG. 10, and more discrete instructions are now given to control the motion of the endoscope. It is important that all of the tumor tissue is destroyed, but if the laser beam destroys tumor tissue only in a plane perpendicular to the laser beam, a small step on the side of the tumor in each plane will remain, as shown in FIG. 9, which also needs to be irradicated if the operation is to be successful. Accordingly, the discrete laser beam 4, is used for this purpose, and is best illustrated by referring to FIG. 10. The 'step' of remaining tumor tissue in a scan plane is further divided into a number of 'discrete' scan planes, the width of which are a division of the width of laser beam 3, as shown in FIG. 10. Each 'discrete' scan plane is irradicated in the same manner as previously described, wherein, laser beam 4, is directed to either rotate or oscillate in a particular 'discrete' scan plane, wherein, the number of rotations or oscillations will increase as the 'step' of the tumor tissue becomes deeper. Another method for vaporizing tumor tissue in each scan plane is to alternately sweep the laser beam between points lying on the contour of the scan plane, wherein, the profile of each scan plane is analyzed by image processing algorithims to develope a set of instructions for oscillating the laser beam between angles corresponding to points on the contour of the scan plane. For example, the tumor tissue lying between D3 and A1 in FIG. 11b, would be vaporized by having the laser beam oscillate from one point on the scan contour to another point on the scan contour so as to vaporize successive layers of tumor tissue at gradually increasing radial distances from the center of the endoscope.

There is one area of the tumor which has not been addressed, and that is the tumor area around the cored hole made thru the tumor between the end of the endoscope and the edge of laser beam 3. This area can not be reached unless the end of the endoscope is pressed into the contiguous brain tissue at the end of the endoscope, and the 'discrete' laser beam 4, is used to irradicate the tumor tissue in this area. However, the 'discrete' laser beam 4, is more easily used to to irradicate the tumor tissue lying in the opposite and similar area behind the last scan plane irradicated.

After the whole procedure has been completed, the endoscope is retracted, and the patient is then moved by trolley back to the CAT or MRI scanner to search for any tumor residue, and to see how accurately the tumor was removed. If all is well, the tumor bed can be irrigated with a clear solution and then pumped out thru the guide tube, or it might even be possible to treat the bed of the tumor with a chemotherapy drug, if the tumor was malignant.

It should now be apparent that the whole procedure is very dependent upon the accuracy of CAT or MRI brain scanners, image processing techniques, and computer analysis to produce a program for directing the rotational and oscilatory motion of the endoscope in each scan plane of the tumor. However, once these programs are determined, the entire operation would be automatic, except that provision would be made for the neurosurgeon to interupt the operation any time at his discretion.

The actual amount of brain damage that would occur with this method is minimal, because the area of the brain damaged would only be the width of the knife by the length of the cut thru the brain tissue, and in many areas of the brain, this may produce hardly any damage to vital brain tissue at all. But as mentioned previously, the best point at which to insert the knife would be determined by the neurosurgeon.

Although the apparatus of the Endoscopic Surgical Laser is primarily intended for removing brain tumors, it is possible to use the same apparatus for removing tumors in other parts of the body. The apparatus and technique could also be used in other applications, such as coring out irregular shaped cavitys in various solid materials. Various modifications and improvements within the scope of the invention could also be made, such as the addition of a light source located in the end of the endoscope to illuminate the inside of the tumor cavity for viewing. From the foregoing description, it should be apparent that the Endoscopic Surgical Laser possesses many advantages over surgical techniques heretofore developed and currently in use for removing brain tumors, in that it is considerably less invasive into the brain then presently used surgical procedures for removing deep seated tumors. Plus the reliability and accuracy of presently developed technologies on which the Endoscopic Surgical Laser relys upon, affords further assurance that removal of tumors in the brain can be accomplished with this apparatus with great accuracy, and with minimum neurological damage to the patient.

I claim:

1. An apparatus for precisely positioning and rotating a beam of laser light comprising:

an endoscope including means to deliver laser light and deflect said laser light at an angle to a longitudinal axis of the endoscope, and;

an actuator tube, wherein said actuator tube has a longitudinal axis, and;

connection means for connecting one end of said actuator tube to a caudal end of said endoscope, wherein said longitudinal axis of said endoscope is coaxial with said longitudinal axis of said actuator tube, and;

a gear, suitably mounted on said actuator tube, said gear having its axis of rotation coaxial with said longitudinal axis of said actuator tube, and;

rotational means, for transmitting rotary motion to said gear suitably mounted on said actuator tube, and;

a laser beam producing means, for producing an elongated beam of laser light, wherein said elongated beam of laser light has a longitudinal optical axis coaxial with said longitudinal axis of said actuator tube, and;

a slidable connection means for slidably connecting said means for producing an elongated beam of laser light with one end of said actuator tube, and;

positioning means, for axially positioning said actuator tube along said longitudinal optical axis of said means for producing an elongated beam of laser light, and;

positioning means connection means, for connecting said positioning means to said actuator tube, wherein said positioning means connection means includes a means for allowing rotation of said actuator tube, whereby, the deflected beam of laser light can be precisely positioned along the longitudinal optical axis of the elongated beam of laser light and precisely rotated about the longitudinal optical axis of the elongated beam of laser light.

2. The apparatus of claim 1, wherein, said actuator tube has a flange suitably mounted on the outside diameter of the actuator tube.

3. The apparatus of claim 1, wherein, said rotational means is a electrical stepping motor having an output shaft, and a pinion gear is mounted on said output shaft that engages said gear suitably mounted on said actuator tube.

4. The apparatus of claim 1, wherein, said positioning means is a electrical step motor positioner having an output shaft.

5. The apparatus of claim 2, wherein, said means for allowing rotation of said actuator tube, is a circular slot at the end of said positioning means output shaft that engages said flange formed on the outside diameter of the actuator tube.

6. An apparatus for vaporizing a brain tumor comprising:

a surgical endoscope adapted to be inserted into a cored hole made thru a brain tumor said surgical endoscope including means to deliver and deflect a laser beam with respect to a longitudinal axis of the surgical endoscope such that the laser beam may be selectively positioned and rotated to vaporize said brain tumor and;

a guide tube, where said guide tube is adapted to be inserted into an incision made through a patient's brain, and said surgical endoscope is placed within said guide tube, and;

an actuator tube, wherein said actuator tube has a longitudinal axis, and;

connection means, for connecting one end of said actuator tube to a caudal end of said surgical endoscope, wherein said longitudinal axis of said surgical endoscope is coaxial with said longitudinal axis of said actuator tube, and;

a gear, suitably mounted on said actuator tube, said gear having its axis of rotation coaxial with said longitudinal axis of said actuator tube, and;

rotational means, for transmitting rotary motion to said gear suitably mounted on said actuator tube, and;

a laser beam producing means, for producing an elongated beam of laser light, wherein said elongated beam of laser light has a longitudinal optical axis coaxial with said longitudinal axis of said actuator tube, and;

a slidable connection means for slidably connecting said means for producing an elongated beam of laser light with one end of said actuator tube, and;

positioning means, for axially positioning said actuator tube along said longitudinal optical axis of said means for producing an elongated beam of laser light, and;

positioning means connection means, for connecting said positioning means to said actuator tube, wherein said positioning means connection means comprises a means for allowing, rotation of said actuator tube, whereby, the deflected laser beam is positioned within said brain tumor at select planes angularly disposed to the longitudinal axis of the surgical endoscope, and selectively rotated to vaporize the tumor tissue lying in each select plane.

7. The apparatus of claim 6, wherein, said connection means at one end of said actuator tube is a female spline formed in an inside diameter of one end of said actuator tube.

8. An apparatus for vaporizing a brain tumor by positioning a laser beam that is deflected at an angle to a longitudinal axis of a surgical endoscope, at select scan planes within the brain tumor, then selectively rotating the deflected laser beam thru predetermined angles to vaporize the tumor tissue lying in each select scan plane, said apparatus comprising;

a surgical endoscope, wherein, said surgical endoscope has a longitudinal axis, and;

a laser beam producing means, for producing an elongated beam of laser light, wherein, said elongated beam of laser light has a longitudinal optical axis coaxial with said longitudinal axis of said surgical endoscope, and;

a laser beam deflecting means, for deflecting said elongated beam of laser light at an angle to said longitudinal axis of said surgical endoscope, wherein, said laser beam deflecting means is suitably mounted adjacent one end of said surgical endoscope, and;

image producing means, for producing images of said select scan planes within said brain tumor, and;

positioning means, for positioning said deflected beam of laser light at said select scan planes within the brain tumor, and;

rotational means, for rotating said deflected beam of laser light about said longitudinal optical axis of said laser beam producing means, and;

image processing computer means, for directing the positioning and rotational means by analyzing the images of said select scan planes within the brain tumor using image processing techniques, wherein, said image processing computer means is electrically connected to said image producing means and said positioning and rotational means, whereby, said deflected beam of laser light is positioned at said select scan planes within the brain tumor and rotated at angles determined by said image processing computer means to vaporize the brain tumor tissue lying in each of said select scan planes.

9. The apparatus of claim 8, wherein, said image producing means is a magnetic resonance imaging scanner.

10. The apparatus of claim 8, wherein, said rotational means is an electrical stepping motor that includes means for transmitting rotary motion to said surgical endoscope.

11. The apparatus of claim 8, wherein, said positioning means is an electrical linear stepping motor positioner that includes means for connecting said electrical linear stepping motor positioner to said surgical endoscope.

\* \* \* \* \*

(12) EX PARTE REEXAMINATION CERTIFICATE (8086th)
United States Patent
Shaunnessey (10) Number: US 5,823,941 C1
(45) Certificate Issued: Mar. 15, 2011

(54) APPARATUS FOR DIRECTING THE MOVEMENT OF AN ENDOSCOPIC SURGICAL LASER ESPECIALLY FOR USE IN VAPORIZING BRAIN TUMORS (75) Inventor: Jerome Shaunnessey, Aurora, IL (US)

(73) Assignee: Jerome Shaunnessey, Port Richey, FL (US)

Reexamination Request:
No. 90/009,421, Mar. 2, 2009

Reexamination Certificate for:
Patent No.: 5,823,941
Issued: Oct. 20, 1998
Appl. No.: 08/553,767
Filed: Oct. 23, 1995

(51) Int. Cl.
*A61B 18/20* (2006.01)
*A61B 18/24* (2006.01)
*A61B 18/00* (2006.01)
*A61B 19/00* (2006.01)

(52) U.S. Cl. .................. 600/108; 606/17; 606/18
(58) Field of Classification Search .............. None
See application file for complete search history.

(56) References Cited

U.S. PATENT DOCUMENTS 4,469,098 A 9/1984 Davi 4,760,840 A 8/1988 Fournier, Jr. et al.
5,222,953 A 6/1993 Dowlatshahi

FOREIGN PATENT DOCUMENTS

FR 2681522 3/1993

OTHER PUBLICATIONS

Federico Moure and Lucia Zamorano, Computer Assisted Volumetric Resections of Intracranial Lesions, Proceedings of Society of Photographic Instrumentation Engineers, 1993, pp. 260–278, vol. 1894, USA.

*Primary Examiner* — Catherine S. Williams (57) ABSTRACT

An apparatus for removing brain tumors by vaporizing the tumor tissue with a laser beam in select scan planes of the tumor. A cored hole through the tumor is made by the laser beam, and an endoscope is inserted through the cored hole, which has a mirror mounted at a 45 degree angle near the end of it and mounted within it, that is capable of reflecting the laser beam at a 90 degree angle. The endoscope is inserted all the way through the cored hole, and sucessive scans of the brain tumor are taken perpendicular to the endoscope. The endoscope is then moved axially to position the 45 degree mirror at each scan plane, and the reflected laser beam is then rotated and also oscillated between calculated angles to vaporize the tumor tissue in each scan plane, until the entire brain tumor is vaporized by the laser beam. During this procedure the gas being produced by vaporization of the tumor tissue is suctioned out through the interior of the endoscope.

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 1-7 is confirmed.

Claims 8-11 are cancelled.

New claims 12-14 are added and determined to be patentable.

*12. An apparatus for vaporizing a brain tumor by positioning a laser beam that is deflected at an angle to a longitudinal axis of a surgical endoscope, at select scan planes within the brain tumor, then selectively rotating the deflected laser beam thru predetermined angles to vaporize the tumor tissue lying in each select scan plane, said apparatus comprising;*

*a surgical endoscope, wherein, said surgical endoscope has a longitudinal axis, and;*

*a laser beam producing means, for producing an elongated beam of laser light, wherein, said elongated beam of laser light has a longitudinal optical axis coaxial with said longitudinal axis of said surgical endoscope, and;*

*a laser beam deflecting means, for deflecting said elongated beam of laser light at an angle to said longitudinal axis of said surgical endoscope, wherein, said laser beam deflecting means is suitably mounted adjacent one end of said surgical endoscope, and;*

*image producing means, for producing images of said select scan planes within said brain tumor, and;*

*positioning means, for positioning said deflected beam of laser light at said select scan planes within the brain tumor, and;*

*rotational means, for rotating said deflected beam of laser light about said longitudinal optical axis of said laser beam producing means, and;*

*image processing computer means, for directing the positioning and rotational means by analyzing the images of said select scan planes within the brain tumor using image processing techniques, wherein, said image processing computer means is electrically connected to said image producing means and said positioning and rotational means, whereby, said deflected beam of laser light is positioned at said select scan planes within the brain tumor and rotated at angles determined by said image processing computer means to vaporize the brain tumor tissue lying in each of said select scan planes, wherein said image processing computer means outputs electrical signals, based on said analyzing, to said positioning means, to said rotational means, or both, to position, or to rotate, or both, said deflected beam of laser light at said select scan planes within said brain tumor.*

*13. The apparatus of claim 9 further comprising a guide tube adapted for insertion into a hole through a patient's skull, said guide tube made of material that insures substantially no interference occurs when said guide tube is placed in the magnetic field of said magnetic resonance imaging scanner.*

*14. The apparatus of claim 9 wherein said magnetic resonance imaging scanner includes a magnet for producing a magnetic field, and said surgical endoscope is adapted to be inserted into a guide tube that is adapted for insertion into a hole through a patient's skull, said surgical endoscope and said guide tube being made of materials that insure substantially no interference occurs when said guide tube and surgical endoscope are placed in the magnetic field of said magnetic resonance imaging scanner.*

\* \* \* \* \*